United States Patent [19]
Welch et al.

[11] Patent Number: 5,302,264
[45] Date of Patent: Apr. 12, 1994

[54] CAPILLARY ELETROPHORESIS METHOD AND APPARATUS

[75] Inventors: Brenton P. Welch, Los Gatos; Barry M. Bredt, Berkeley, both of Calif.

[73] Assignee: Scientronix, Inc., San Jose, Calif.

[21] Appl. No.: 939,061

[22] Filed: Sep. 2, 1992

[51] Int. Cl.⁵ .................. G01N 27/26; G01N 27/447
[52] U.S. Cl. ............... 204/180.1; 204/299 R
[58] Field of Search ........... 204/299 R, 180.1, 182.8, 204/183.3

[56] References Cited

U.S. PATENT DOCUMENTS

| | | | |
|---|---|---|---|
| 3,537,585 | 11/1970 | Waters | 210/198.2 |
| 3,705,845 | 12/1972 | Everaets | 204/183.3 |
| 3,822,197 | 7/1974 | Nees et al. | 204/299 R |
| 3,998,719 | 12/1976 | Deml et al. | 204/183.3 |
| 4,594,064 | 6/1986 | Anderson | 204/299 R |
| 4,698,142 | 10/1987 | Murio et al. | 204/182.3 |
| 4,810,456 | 3/1989 | Bente, III et al. | 204/180.1 X |
| 4,867,855 | 9/1989 | Burton | 204/182.8 |
| 4,897,169 | 1/1990 | Bier et al. | 204/182.8 |
| 4,906,344 | 3/1990 | Hjerten | 204/182.8 |
| 4,911,816 | 3/1990 | Love et al. | 204/299 R |
| 4,936,974 | 6/1990 | Rose et al. | 204/299 R |
| 4,963,236 | 10/1990 | Rodkey et al. | 204/183.2 |
| 4,997,536 | 3/1991 | Ohms et al. | 204/180.1 |
| 4,997,537 | 3/1991 | Karger et al. | 204/182.8 |
| 5,015,350 | 5/1991 | Wiktorowicz | 204/180.1 |
| 5,019,236 | 5/1991 | Young | 204/299 R |
| 5,045,172 | 9/1991 | Guzman | 204/299 R |
| 5,053,115 | 10/1991 | Weinberger et al. | 204/299 R |
| 5,061,355 | 10/1991 | Rose, Jr. | 204/182.8 |

FOREIGN PATENT DOCUMENTS

| | | | |
|---|---|---|---|
| 329341 | 8/1989 | European Pat. Off. | 204/299 R |
| 339781 | 11/1989 | European Pat. Off. | 204/299 R |
| 395796 | 11/1990 | European Pat. Off. | 204/299 R |

OTHER PUBLICATIONS

Compton, S. W., BioTechniques, "Capillary Electrophoresis", vol. 6, No. 5, pp. 432–440 (1988).
Datta, Ravindra, Biotechnol. Prog., "Theoretical Evaluation of Capillary Electrophoresis Performance", vol. 6, No. 6, pp. 485–493, (1990).
Datta, Ravindra et al., AICHE Journal, "Electrokinetic Dispersion in Capillary Electrophoresis", vol. 36, No. 6, pp. 916–926, (Jun. 1990).
Gordon, Manuel J. et al., Science, "Capillary Electrophoresis", vol. 242, pp. 224–228, (1988).
Hjerten, Stellan et al., Journal of Chromatography, "Adaptation of the Equipment for High-Performance Electrophoresis to Isoelectric Focusing", 346, pp. 265–270 (1985).
Hjerten, Stellan et al., Journal of Chromatography, "Carrier-Free Zone Electrophoresis, Displacement Electrophoresis and Isoelectric Focusing in a High-Performance Electrophoresis Apparatus", 403, pp. 47–61 (1987).

(List continued on next page.)

*Primary Examiner*—John Niebling
*Assistant Examiner*—John S. Starsiak, Jr.
*Attorney, Agent, or Firm*—John J. Leavitt; William A. Blake

[57] ABSTRACT

A capillary electrophoresis method and apparatus (10) are disclosed in which pressure or vacuum is selectively applied to an outlet end (16) of the capillary tube (12) during sample loading, sample separation and sample mobilization past a detector (34). The vacuum can be used to load a sample mixture from the reservoir (20) quickly into the capillary tube (12), and then also move the sample quickly toward a detector (34) once it has been separated. When a voltage is applied across the capillary tube (12) to effect separation of analytes in the mixture sample, the pressure or vacuum can be selectively controlled as desired to either augment or oppose the effects of electroosmotic flow, and thereby enhance the sample separation. The pressure or vacuum can be adjusted during any phase of the operation and feedback circuitry (110) can be employed to control the flow rate of a sample through the capillary tube automatically.

6 Claims, 3 Drawing Sheets

OTHER PUBLICATIONS

Honda, Susumu et al., Journal of Chromatography, "Evaluation of an Automatic Siphonic Sampler for Capillary Zone Electrophoresis", 404, pp. 313–320 (1987).

Huang, Xiaohua et al., Analytical Chemistry, "Bias in Quantitative Capillary Zone Electrophoresis Caused by Electrokinetic Sample Injection", vol. 60, No. 4, pp. 375–377 (Feb. 15, 1988).

Lee, Cheng S. et al., Analytical Chemistry, "Factors Affecting Direct Control of Electroosmosis Using an External Electric Field in Capillary Electrophoresis", vol. 63, No. 15, pp. 1519–1523 (Aug. 1, 1991).

Linhares, Michael C. et al., Analytical Chemistry, "Use of an On-Column Fracture in Capillary Zone Electrophoresis for Sample Introduction", vol. 63, No. 18, pp. 2076–2078 (Sep. 15, 1991).

Mazzeo, Jeff R. et al., Analytical Chemistry, "Capillary Isoelectric Focusing of Proteins in Uncoated Fused-Silica Capillaries Using Polymeric Additives", vol. 63, No. 24, pp. 2852–2857 (Dec. 15, 1991).

Zhu, Mingde et al., Journal of Chromatography, "Optimizing Separation Parameters in Capillary Isoelectric Focusing", vol. 559, pp. 479–488 (1991).

CAPILLARY ELETROPHORESIS METHOD AND APPARATUS

BACKGROUND OF THE INVENTION

The present invention relates in general to a method and apparatus for controlling liquid flow in capillary electrophoresis (CE).

CE is a known technique for effecting separation of a mixture of analytes in which a voltage is applied across a capillary containing a sample, and the resulting electric field causes electrophoretic flow of charged molecular species in the sample. This technique can be utilized, for example, to separate proteins having different charges because the applied electric field will cause the differently charged proteins to travel at different velocities, thereby causing separation of them along the length of the capillary.

The charged ions have an electrophoretic mobility which is proportional to the magnitude of their charge density, and this is one of the major forces for causing separations in CE. Another force results from the ionization of silanol groups along the wall of the capillary. In particular, when a fused silica capillary is employed and is filled with an aqueous solution having a pH above approximately 2, the surface silanol groups will become ionized, resulting in a negative charge on the wall of the capillary. Cations (positively charged ions) of the aqueous solution are attracted to the negatively charged capillary wall thereby forming an electrical double layer at the capillary wall solute interface. When a voltage is applied across the capillary, these cations flow towards a cathode end of the capillary, thereby resulting in a bulk flow of fluid in this direction. This bulk flow is referred to as electroendosmosis or electroosmotic flow, otherwise known as EOF.

Electrophoretic mobility and EOF are therefore the two major electrical forces in CE. This can be illustrated by assuming the typical situation where the EOF is greater than the electrophoretic mobility of the materials in the sample to be analyzed. Cations are electrophoretically mobilized toward the cathode end of the capillary, and their electrophoretic mobility towards the cathode is enhanced by the EOF. On the other hand, anions (negatively charged ions) are electrophoretically attracted toward the anode end of the capillary, but since the EOF is greater than the electrophoretic mobility, the anions net movement is toward the cathode with the bulk flow. In this situation, the order of flow of analytes passing a detector positioned at the cathode end of the capillary will be cations, then neutral species, then anions. It will be understood that the higher the magnitude of the EOF relative to the electrophoretic mobility, the more close together the various analytes will be as they pass the detector. Thus, if the effects of the EOF can be reduced, the analytes can be more spread out, thereby increasing the resolution of the separation.

A number of problems are presented in conducting separations with CE. First, in order to effect a separation of a mixture of analytes, some method must be employed to load the analyte mixture sample into the capillary. The most common methods are electrokinetic and hydrodynamic sample loading. Electrokinetic sample loading, also called electrokinetic injection or electromigration, utilizes both electrophoretic and electroosmotic flow to introduce a sample into the capillary. The inlet end of the capillary and a power supply's anode are placed into a sample containing vial, and a voltage is applied across the capillary for a period of time. The strength and duration of the resulting electric field ideally determine the amount of the sample introduced into the capillary; however, there is a bias in this method of sample introduction. Briefly, cations are introduced into the capillary by virtue of both electrophoretic mobility and EOF. However, uncharged species and anions are introduced into the capillary by virtue of only EOF since their electrophoretic mobility is either zero in the case of uncharged species, or in the direction of the anode in the case of anions. Thus, anions migrate into the capillary more slowly than uncharged species because of the electrical attraction of the anions toward the anode. Therefore, the different electrophoretic mobilities of the analytes arising from their different charge densities is a source of bias in sample loading by electrokinetic injection. Another bias occurs because different electrolyte buffer solutions have different electrophoretic and EOF rates, resulting in different amounts of sample being injected.

Several approaches to eliminating these sources of bias in electrokinetic injection have been reported, all of which implicitly aim to decouple electrophoretic flow from EOF, thereby accomplishing sample introduction through EOF alone. This decoupling has in all cases been achieved through approaches involving alterations to the capillary structure itself, such as by introducing porous glass or a frit, coupling to an additional capillary or fracturing the capillary. These approaches all require specialized capillary manufacturing techniques, are rather complex and labor intensive, and do not address the problems associated with the changes in the electrolyte buffer solution.

A nonelectrical sample loading method, such as hydrodynamic sample loading, avoids all of the problems associated with electrokinetic sample loading. All hydrodynamic sample loading methods involve, by one means or another, a pressure differential between the inlet and outlet ends of the capillary. This can be accomplished simply by raising the inlet end of the capillary above the outlet end, or through the use of either a pressure pump or syringe pump at the inlet end of the capillary, or a vacuum pump at the outlet of the capillary. Most known hydrodynamic sample loading methods are rather bulky and expensive to implement. Further, all of these methods suffer from potential band broadening with an attendant loss of resolution if the pressure differential is so large, or the inside diameter of the capillary is so small, that the injection front is distorted. For example, in one experiment with an optimized commercial CE system using pressures as low as 0.497 psi for sample loading, the experimentally determined injected volume per unit time deviated from a calculated theoretical value by 6.1%.

Another problem with conventional CE systems is that of controlling the effects of the EOF. Because the EOF is a source of a zone broadening in free zone CE, or disturbs focused zones in isoelectric focusing CE, many investigators have attempted to eliminate EOF entirely. Reducing the EOF below zero, i.e., reversing the direction of the EOF, or increasing the EOF may be advantageous in some applications such as micellar electrokinetic capillary chromatography (MECC) because resolution may be increased and analysis time reduced.

A number of techniques have been employed to increase, decrease or eliminate the effects of the EOF. One such technique involves coating the inner surface of the capillary with a material whose charge is different from that of the uncoated capillary. Use of an electrically neutral coating material would eliminate the surface charge that gives rise to EOF, while use of the material whose charge is more negative than that of the inner surface of the capillary would increase the EOF. On the other hand, use of a material whose charge is positive would reverse the direction of the EOF. However, the use of coatings to change the EOF has drawbacks. In particular, the coatings degrade with use over time and suffer from the complexity involved in the coating procedures. Also, these methods all result in a capillary with a changed, but not adjustable EOF.

Another technique for changing the EOF involves the use of electrolyte buffer additives which cause Coulombic repulsion between the capillary surface and the analytes to reduce the EOF. Other additives may be used to increase or reverse the EOF. Unfortunately, use of such additives presents the possibility that the additive may adversely affect the material to be analyzed. Further, the use of these methods once again does not provide for adjustment of the EOF during CE. Yet another method for changing or controlling the EOF involves the manipulation of the bulk flow through the application of electric fields or temperature gradients, although these methods tend to be overly complex.

A third problem in conventional CE systems is presented by the need to move the sample material past a detector of some kind after the analytes therein have been separated. More particularly, once the individual components in the analyte mixture sample have been separated, they are caused to flow past a detector, such as a UV absorbance, radioactive decay or fluorescence detector, so that some attribute of the component can be sensed thereby. Then the component flows out of the capillary into the reservoir disposed at the outlet end thereof. Electrophoretic mobility, EOF and pressure have all been utilized to achieve this mobilization through the capillary. The same problems associated with sample loading occur in mobilization; namely, electrophoretic mobilization may be biased, EOF is difficult to control and pressure systems have been relatively crude and inaccurate. Once again, none of these approaches allows the real-time control of the rate of mobilization.

An example of the mobilization problem occurs in isoelectric focusing (IEF) CE. In IEF CE, a pH gradient is formed along the length of the capillary and analytes migrate through this gradient until they reach the pH zone where their net charge is zero, and they stop moving. Thus, the EOF needs to be eliminated so that there is no bulk fluid flow. In this manner, an analyte is focused into a zone at its isoelectric point. After the separation is completed in this manner, the zones must be mobilized past a detector, ideally without any disturbance of the focused zones.

For this purpose, an electrophoretic mobilization technique called salt mobilization has been developed and commercialized. Once focusing is completed, the electric field is turned off, salt is added either to the anode or cathode buffer reservoirs and the field is reapplied, thus causing an excess of either $H^+$ or $OH^-$ to enter the capillary thereby changing the pH gradient and causing migration toward the cathode or anode as the case may be. This system is ideally set up so that the pH gradient will flow past the detector window on its way toward the electrode. This procedure suffers from the need to perform the multiple steps discussed above. In addition, the focused zones are susceptible to diffusion while the field is turned off and to an electrophoretic bias during the electrically driven mobilization. Hence, reproducibility and resolution are often adversely affected.

Another technique used for mobilization in IEF CE is to sharply reduce, but not eliminate, the EOF, such as through the inclusion of methyl cellulose in the electrolyte buffer. The reduced EOF can then be employed for mobilization once the separation is completed, however, this technique requires a compromise between the separation resolution and the mobilization speed. Further, the rate of mobilization cannot be adjusted with this technique.

SUMMARY OF THE INVENTION

In view of the foregoing drawbacks to conventional CE systems and techniques, what is clearly needed is a new CE method and apparatus whereby sample loading and mobilization can be easily and quickly accomplished and the effects of the EOF can be increased, decreased or eliminated as desired during a separation.

In view of the foregoing, it is an object of the present invention to provide a CE method and apparatus in which a sample to be separated can be quickly and easily loaded into a capillary, and then mobilized past a detector once separation of the analytes in the sample is completed.

It is another object of the present invention to provide an improved CE method and apparatus in which the effects of the EOF can be changed, i.e., increased, decreased or eliminated, as desired during a separation.

These and other objects of the present invention are achieved through use of a system by which pressure and vacuum (negative pressure) are selectively and controllably applied to a sample capillary so that sample loading and mobilization can be easily and precisely controlled, and the effects of the EOF can be easily and precisely increased, reduced or eliminated, as desired. The system preferably employs a combination pressure/vacuum pump in conjunction with a plurality of regulators and valves connected to one end of the capillary. Through selective application of positive or negative pressure to the capillary, a sample can be loaded therein, separated and then mobilized past a detector.

In a preferred embodiment of the invention, the pressure/vacuum pump is a dual-head diaphragm design in which one head supplies vacuum and the other head supplies pressure. The two heads are each connected through a pair of regulators, one for precisely controlling very low pressures or vacuums, and another for regulating higher magnitude pressures or vacuums. Electronically controlled valves are employed for selectively connecting the desired regulated pressure or vacuum to a sealed outlet reservoir in which the outlet end of the capillary tube is disposed.

In one typical operational mode of the system, a relatively high vacuum is applied to the outlet reservoir to facilitate sample loading into the capillary from an inlet reservoir. Once the sample is loaded and sample separation is ready to begin, a precisely controllable pressure is applied to the outlet reservoir to counteract the effects of the EOF as desired during sample separation. When the sample is separated, the pressure is reduced to allow a low mobilization rate of the separated sample past the detector.

In the above described embodiment of the invention, the applied pressure or vacuum is controlled by manual adjustment of the pressure and vacuum regulators and valves. However, in another embodiment of the invention employing microprocessor control, the pressure and vacuum can be automatically controlled in response to measured flow in the capillary tube. To achieve this, a special flow meter is positioned adjacent to a portion of the capillary tube, and provides flow proportional signals to the microprocessor. The microprocessor also receives inputs from a data entry terminal so that it can be programmed to respond to the flow signals as desired, and generate control signals for actuating the valves and regulators. The flow meter is specially designed to detect the very low flow rates present in the very small diameter capillary tube, and in one preferred embodiment, employs a pulsed light source to periodically illuminate the flow, and cause a special marker solution therein to fluoresce. Light detectors are positioned a predetermined distance on either side of the light source so that the flow rate can be determined by measuring the time it takes the fluoresced portion of the sample to travel from the light source to either detector.

BRIEF DESCRIPTION OF THE DRAWINGS

The foregoing and additional objects, features and advantages of the present invention will become apparent from the following detailed description of a preferred embodiment thereof, taken in conjunction with the accompanying drawings in which.

DETAILED DESCRIPTION OF THE PREFERRED EMBODIMENTS

Figure 1:
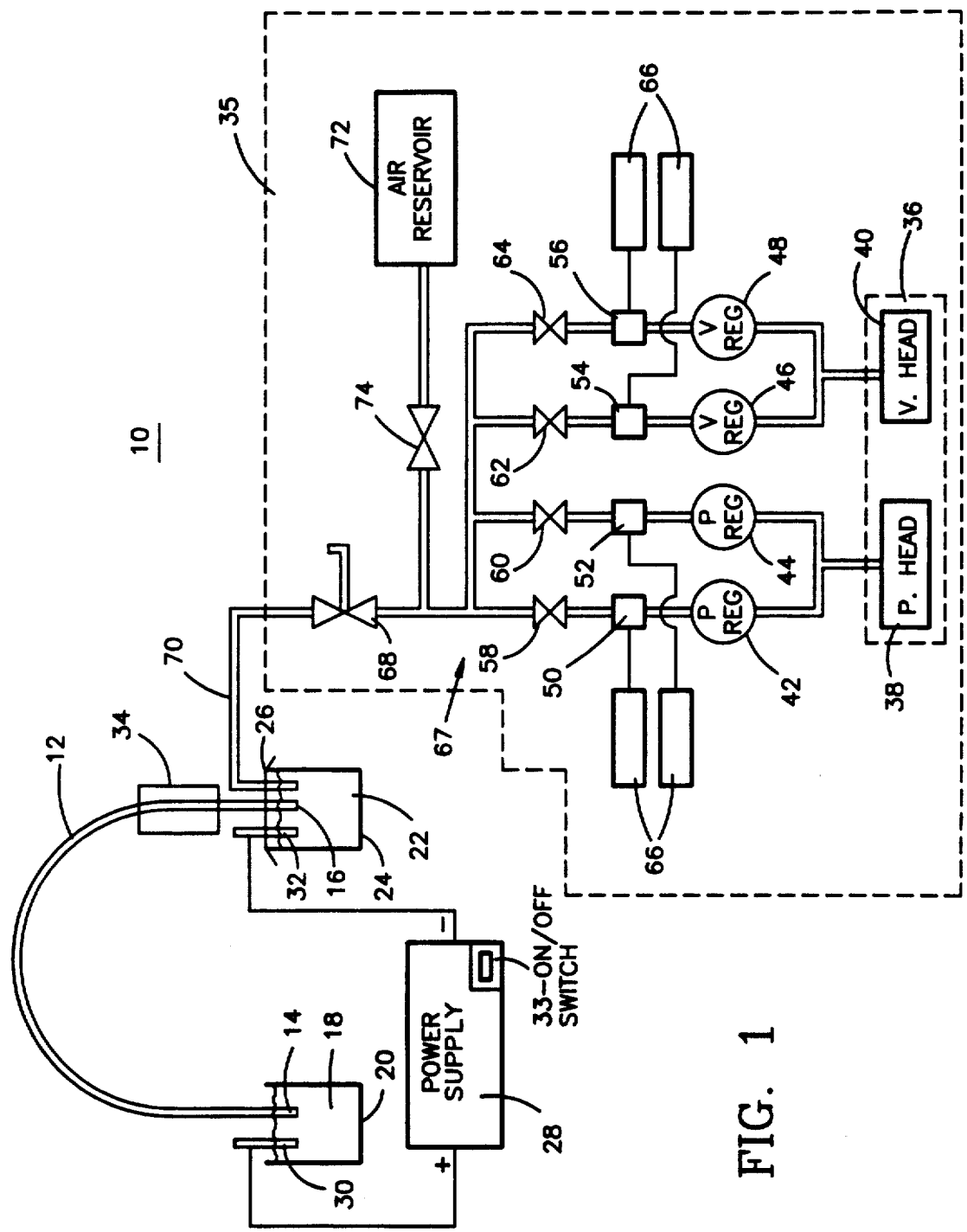
FIG. 1 is a schematic block diagram of a CE system constructed in accordance with the present invention.

Turning now to a more detailed consideration of a preferred embodiment of the present invention, FIG. 1 illustrates a CE system 10 including a capillary tube 12 having an anode inlet end 14 and a cathode outlet end 16. The inlet end 14 of the capillary tube 12 is in communication with an analyte mixture 18 contained in a first reservoir 20 which is open to the atmosphere. The outlet end 16 of the tube 12 is in communication with an analyte mixture 22 contained in a second reservoir 24 which is sealed with a septum 26.

As is conventional, a high voltage power supply 28 is connected across the capillary tube 12 through the analyte mixtures 18 and 22 by means of an anode 30 and a cathode 32 to supply a high voltage which causes electrophoretic flow of ions in the mixture sample contained in the capillary tube 12. Since different analytes in the mixture possess different electrical charges and therefore have different electrophoretic mobilities, the application of the high voltage will cause movement of the different analytes at different velocities, thereby effecting a separation of the analytes along the length of the capillary tube 12. The power supply 28 includes an on/off switch 33 which allows selective application of voltage across the capillary tube 12.

Once the analytes in a mixture sample have been separated, the separated sample components move past a detector 34 toward the outlet end 16 of the tube 12 and into the second reservoir 24. The detector 34 can be any suitable detector means for sensing analyte characteristics, such as a UV absorbance detector, radioactive decay detector or fluorescence detector.

A key feature of the CE system 10 resides in the provision of a pressure/vacuum supply system 35 including a controllable combination pressure/vacuum pump 36 for selectively and precisely applying positive pressure or vacuum (negative pressure) to the second, sealed reservoir 24 to control sample movement through the capillary tube 12. The pressure/vacuum pump 36, which by way of example can be an ASF Model 7010 ZD/V, includes a pressure head 38 for supplying pressure and a vacuum head 40 for supplying vacuum. The output from the pressure head 38 is split between a low pressure regulator 42 and a high pressure regulator 44 connected in parallel. The low pressure regulator 42 is set to regulate pressure over a range of approximately 0.020 to 1.500 PSI, while the high pressure regulator 44 is set to regulate pressure over a range of approximately 0.102 to 10.00 PSI. Similarly, the output of the vacuum head 40 is split between a low vacuum regulator 46 and a high vacuum regulator 48 in parallel. Again, the low vacuum regulator 46 is set to regulate vacuum over the range of approximately $-0.020$ to $-1.500$ PSI, while the high vacuum regulator 48 is set to regulate vacuum over the range of approximately $-0.10$ to $-10.00$ PSI. By way of example, each of the regulators 42, 44, 46 and 48 can be an Airtrol Model 4104.

The outputs of the regulators 42, 44, 46 and 48 are each connected through a corresponding pressure transducer 50, 52, 54 and 56 to a respective electrically controllable valve 58, 60, 62 and 64. Each of the pressure transducers 50, 52, 54 and 56 generates an electrical output which is connected to a respective one of a plurality of liquid crystal displays 66. By way of example, the pressure transducers 50 and 54 connected to the regulators 42 and 46 can each be a Sensym Model SCX 01 DN, while the transducers 52 and 56 connected to the regulators 44 and 48 can each be a Sensym Model SCX 05 DN. Each of the valves 58, 60, 62 and 64 can be a Clippard Model EV-2, while each of the displays 66 can be a Sensym Model SCX-LCD.

The outputs from the valves 58, 60, 62 and 64 are combined with a tubing manifold 67 to a single three-way vent valve 68, which in turn is placed in communication with the interior of the sealed second reservoir 24 by means of an outlet tube 70. By way of example, the three-way vent valve 68 can be a Clippard Model EV-3. Also connected to the three-way vent valve 68 by means of the tubing manifold 67 is an air vacuum chamber or reservoir 72. It is employed for maintaining a vacuum or pressure to be applied to the outlet tube 70 for sample loading. The air reservoir 72 enables the atmospheric pressure in the outlet tube 70 and second reservoir 24 to be quickly adjusted during sample loading. Another electronically controlled valve 74 selectively connects the air reservoir 72 to the tubing manifold 67.

Figure 2:
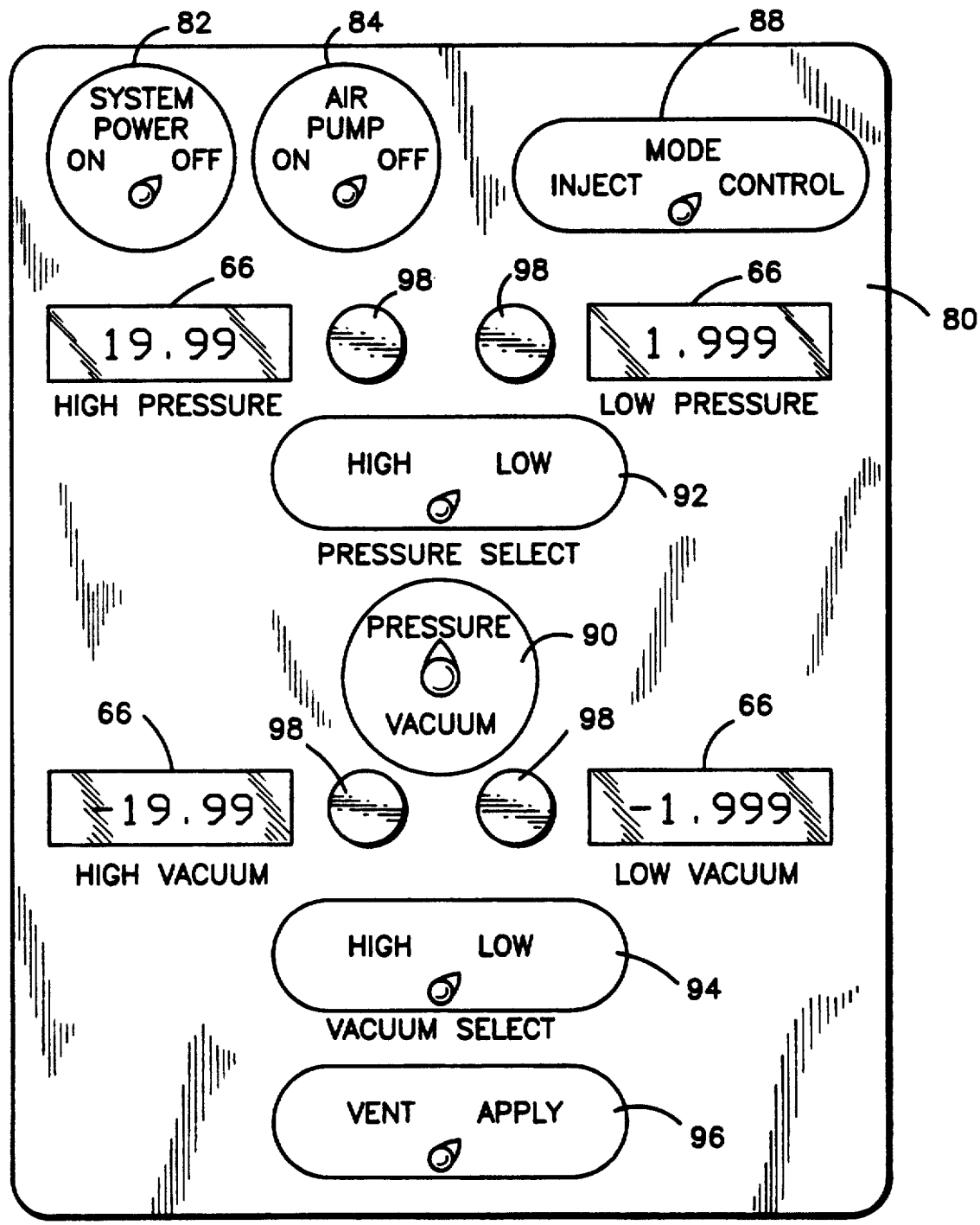
FIG. 2 is an illustration of a control panel for the system of FIG. 1.

Turning now to FIG. 2, a control panel 80 for controlling supply of pressure or vacuum to the second reservoir 24 is illustrated. The panel 80 includes a plurality of on-off control switches including a system power switch 82 for controlling power to the various elements of the pressure/vacuum supply system 35, an air pump switch 84, and a mode control switch 88 for actuating the air reservoir control valve 74 and thereby switching between injection and control modes.

A pressure/vacuum switch 90 selects whether the pressure valves 58 and 60 or vacuum valves 62 and 64 will be actuated, while a high/low pressure switch 92 selects which of the pressure valves 58 or 60 will be actuated, and a high/low vacuum switch 94 selects which of the vacuum valves 62 or 64 will be actuated. Finally, a vent control switch 96 controls operation of the three-way vent valve 68 to selectively connect pressure, vacuum or the atmosphere through the outlet tube 70 to the second reservoir 24.

Also provided on the control panel 80 are four control knobs 98, one for each of the regulators 42, 44, 46 and 48. Each of the knobs 98 is disposed along side a corresponding one of the pressure displays 66, and can be manually turned to adjust the applied pressure or vacuum as desired.

In the operation of the CE system 10, when it is desired to load a sample to be separated from the first reservoir 20 into the capillary tube 12, the pressure/vacuum switch 90 is moved to the vacuum position, the high/low vacuum switch 94 is moved to the low position, and the control knob 98 for the low vacuum regulator 46 is adjusted until the desired injection vacuum is obtained as indicated by the corresponding display 66. At the same time, the mode control switch 88 is moved to the inject position so that the injection air reservoir 72 will be communicated with the low vacuum regulator 46 and will be evacuated to the chosen vacuum magnitude. The vent switch 96 is then moved to the apply position so that the three-way vent valve 68 places the air reservoir 72 and low vacuum regulator 46 in communication with the outlet reservoir 24. The air reservoir 72 is employed to insure that the outlet tube 70 and outlet reservoir 24 will be quickly evacuated when the three-way valve 68 is opened. Typically, a sample can be loaded into the capillary tube 12 in this manner by applying a vacuum of approximately −0.25 PSI for a few seconds.

Once the sample is positioned in the capillary tube 12, voltage is applied by the power supply 28 across the capillary tube 12 through the anode 30 and cathode 32 so that separation of the analytes in the sample will occur. To reduce or counteract the effects of the EOF during the separation, pressure can be applied to the outlet reservoir 24 as desired. If it is desired, for example, to counteract the effects of the EOF, a neutral marker can be injected into the capillary tube 12 ahead of the sample and caused to move to the detector 34 at which point the pressure is adjusted so that the neutral marker is held stationary in the detector window. Since the marker has no charge and is therefore acted upon only by EOF, the stationary position of the neutral marker is an indication that the EOF has been counteracted. Once a sample has been separated, the pressure is reduced in the outlet reservoir 24 so that the separated analytes flow through the capillary tube 12 past the detector 34.

Experiments have been conducted employing the CE system 10 for different types of separations, and promising results have been obtained. In one experiment, a plurality of salt solutions were injected into the capillary so that their anions could be separated. Anions are normally acted upon by the EOF so strongly that they pass the detector before they are noticeably separated. However, by applying a pressure of approximately 1.8 PSI above atmospheric to the outlet reservoir 24, the effects of the EOF were reduced enough that the anions had sufficient time to be separated from one another so that the detector 34 could individually detect them. Similarly, in another experiment, cations, which normally flow toward the inlet end 14 of the capillary tube 12, were caused to flow past the detector 34 by applying a vacuum of −1.4 PSI to the outlet reservoir 24.

In yet another application of the CE system 10, an experiment was conducted employing Micellar Electrokinetic Capillary Chromatography (MECC). MECC is a technique that separates analytes on the basis of their differential ability to partition in and out of micelles present in the capillary in the capillary buffer. A micelle is typically a spherically shaped molecular complex made up of detergent molecules which are arranged such that the hydrophobic part is on the inside of the sphere, and the hydrophilic part is on the outside of the sphere. Analytes that have little charge or are neutral may be separated by MECC. The micelles move through the capillary when a voltage is applied, and an analyte will partition between the inside of the micelle and the buffer outside the micelle, depending upon how hydrophobic the analyte is. An analyte that is very hydrophobic will spend more time inside the micelle, while an analyte that is less hydrophobic will spend less time inside the micelle.

The CE system 10 can be used to increase the resolution in MECC. This is done by opposing the EOF with pressure so that the analytes have more time to partition in and out of the micelles. The increased time will allow the analytes to completely separate in a short capillary. In one experiment, MECC was employed to separate adenine and thymidine. The separation was conducted first with no pressure opposing the EOF, and the result was that both analytes were not completely separated by the time they passed the detector 34. A second experiment was then conducted using a pressure of 0.40 PSI to oppose the EOF, and this time, the analytes were completely separated.

Figure 3:
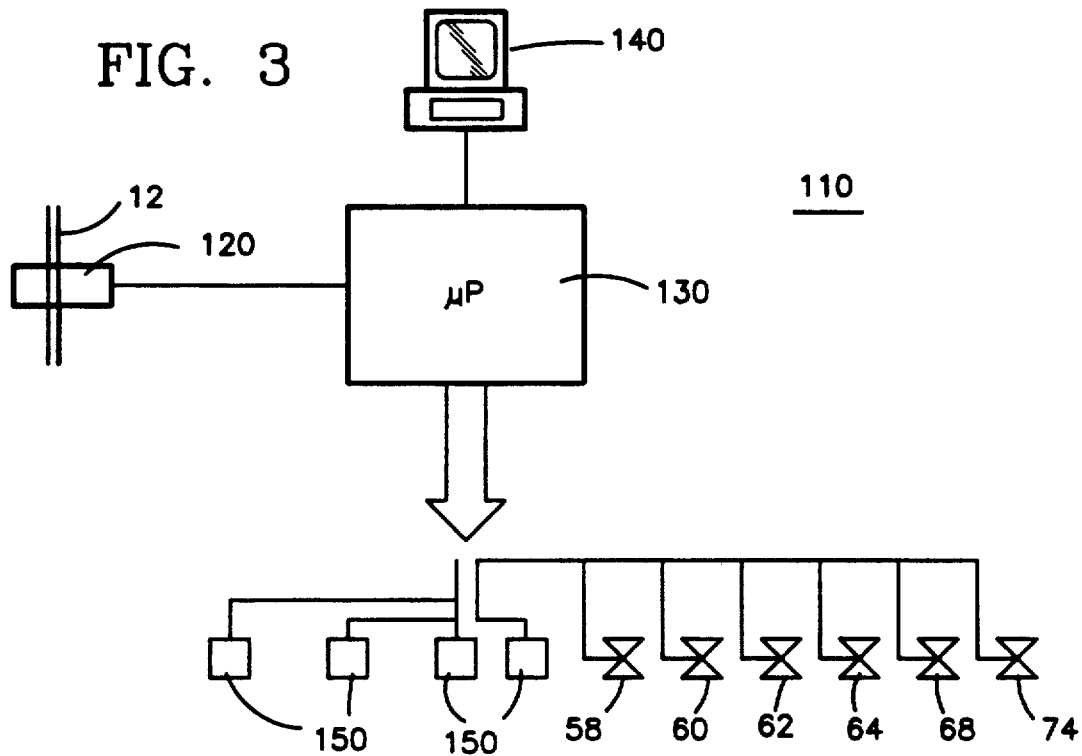
FIG. 3 is a schematic block diagram of a modification to the system of FIG. 1 which provides automatic control of the applied pressure and vacuum in response to the measured flow rate in the capillary.

Although the system of FIGS. 1 and 2 is illustrated as being manually controllable, the system can also be easily modified for automatic operation as illustrated in FIG. 3. In particular, FIG. 3 shows a feedback control circuit 110 for the CE system 10 of FIGS. 1 and 2. The control circuit 110 includes a flow meter 120 for measuring flow in the capillary tube 12 and generating an output to be fed to a microprocessor 130. The microprocessor 130 also receives inputs from a data entry terminal 140 for selecting a desired flow rate. In response to the measured flow rate and the desired flow rate, the microprocessor 130 generates control signals for a plurality of stepper motors or other suitable actuators 150 for adjusting the pressure and vacuum regulators 42, 44, 46 and 48 of FIG. 1. Similarly, the microprocessor 130 generates control signals for actuating the various valves in the pressure and vacuum system of FIG. 1.

Figure 4:
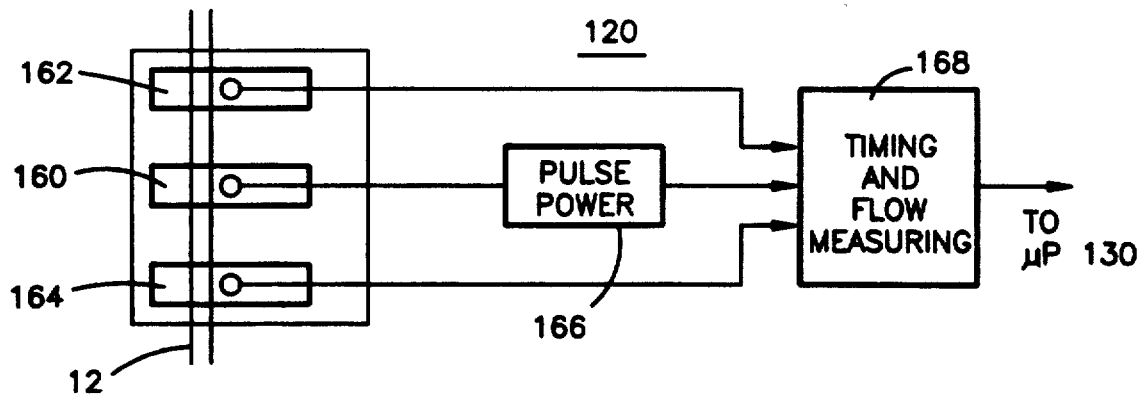
FIG. 4 is an illustration of a flow meter for use in the modification of FIG. 3.

Turning now to FIG. 4, the details of one preferred form of the flow meter 120 are illustrated. Since the capillary tube 12 is very small in diameter and the flow rate of a sample therethrough is very low, a special type of flow meter needs to be employed to sense the flow. The flow meter 120 includes a light source 160 for illuminating the sample in the capillary tube 12, and a pair of light detectors 162 and 164 disposed predetermined distances on either side of the light source 160. A pulse power circuit 166 is connected to the light source 160, and is also connected along with the outputs from the light detectors 162 and 164 to a timing and flow measuring circuit 168.

In the operation of the flow meter 120, a fluorescent marker is added to the sample in the capillary tube 12 so that when the light source 160 is pulsed on, the portion of the sample directly adjacent the light source 160 will fluoresce. Depending on the direction of the flow in the capillary 12, the fluorescing portion of the sample will subsequently pass either the light detector 162 or the detector 164 The timing circuit 168 is employed to measure the elapsed time between the light pulse and the detection of the fluorescing portion of the sample. Since the distance between the light source and the light detectors 162 and 164 is known, the flow rate in the capillary tube 12 can be determined by dividing this distance by the measured elapsed time.

In summary, the present invention provides an improved CE system in which not only can sample loading and mobilization past a detector be accomplished much more quickly and easily than in prior CE systems, but the effects of the EOF can also be easily and precisely increased, decreased or eliminated during sample separation to improve resolution and other aspects of the separation.

Although the present invention has been disclosed in terms of a number of preferred embodiments, it will be understood that numerous modifications and variations could be made thereto without departing from the scope of the invention as defined in the following claims. For example, the pressure or vacuum can be applied to the first reservoir 20 instead of the second reservoir 24. In this case, pressure will be employed for sample loading and mobilization, while vacuum will be employed to counteract the EOF. Other similar modifications or variations could also be made to the other elements of the system as well.

What is claimed is:

1. Apparatus for capillary electrophoresis comprising:
    a capillary tube for separating an analyte sample mixture, said tube including an inlet end for receiving a sample to be separated, and an outlet end for discharging a separated sample;
    means to apply a voltage across said capillary tube to generate an electric field which will cause separation of analytes in a sample;
    means to apply differential pressure to one end of said capillary tube for selectively controlling sample loading, separation and post-separation mobilization, said differential pressure being selectively adjustable over a range of magnitudes including positive, zero and negative magnitudes; and
    detector means positioned near said outlet end of said capillary tube for sensing at least one detectable characteristic of a separated analyte as it is moved in said capillary tube past said detector towards said outlet end.

2. The apparatus of claim 1, further including flow metering means for measuring the flow rate in said capillary tube, and feedback circuitry means connected to said flow metering means and said means to apply pressure, for controlling the applied pressure in response to the measured flow rate in said capillary tube.

3. The apparatus of claim 2, wherein said flow metering means comprises:
    a light source positioned adjacent said capillary tube;
    a first light detector positioned adjacent said capillary tube a predetermined distance along said tube in a first direction from said light source;
    a second light detector positioned adjacent said capillary tube a predetermined distance in a second, opposite direction along said capillary tube;
    a pulse power circuit connected to said light source for intermittently actuating the same to effect fluorescence of a fluorescent marker injected in said capillary tube; and,
    a timing circuit receiving signals from said first and second light detectors and said pulse power circuit for measuring the elapsed time between actuation of said light source to cause a fluorescent marker flowing in said capillary tube to fluoresce and detection of the fluorescent marker by one of said light detectors;
    whereby the flow rate in said capillary tube is determined by measuring the elapsed time.

4. A method for conducting capillary electrophoresis wherein a capillary tube is employed having an inlet end placed in a first reservoir containing an analyte mixture to be separated, an outlet end placed in a second reservoir and a detector means positioned near said outlet end, said method comprising the steps of:
    selectively applying a differential pressure to at least one of said reservoirs to cause a sample of said analyte mixture to flow into said capillary tube;
    applying a voltage across said capillary tube to cause differential movement of analytes in said sample and thereby effect a separation of analytes in said sample along said capillary tube;
    selectively adjusting said applied differential pressure to at least one of said reservoirs to change the effects of electroosmotic flow on said sample during said separation; and
    selectively adjusting said applied differential pressure to at least one of said reservoirs to mobilize the separated sample past said detector means, through said outlet end and into said second reservoir.

5. The method of claim 4, wherein the magnitude of the applied pressure during the analyte separation is selected to oppose the effects of electroosmotic flow in said capillary tube.

6. The method of claim 4, further comprising the step of measuring the flow rate of said sample in said capillary tube, and adjusting the applied pressure in response to said measurement to control the flow rate as desired.

* * * * *